US011559651B2

(12) United States Patent
Orr et al.

(10) Patent No.: US 11,559,651 B2
(45) Date of Patent: Jan. 24, 2023

(54) APPARATUS AND METHOD FOR OXYGEN DELIVERY TO A PATIENT DURING MANUAL VENTILATION

(71) Applicant: Dynasthetics, LLC, Salt Lake City, UT (US)

(72) Inventors: Joseph Orr, Park City, UT (US); Derek Sakata, Salt Lake City, UT (US); Kyle M. Burk, Salt Lake City, UT (US)

(73) Assignee: Dynasthetics, LLC, Salt Lake City, UT (US)

( * ) Notice: Subject to any disclaimer, the term of this patent is extended or adjusted under 35 U.S.C. 154(b) by 1121 days.

(21) Appl. No.: 16/176,959

(22) Filed: Oct. 31, 2018

(65) Prior Publication Data

US 2020/0129719 A1 Apr. 30, 2020

(51) Int. Cl.
*A61M 16/06* (2006.01)
*A61M 16/10* (2006.01)
*A61M 16/20* (2006.01)
*A61M 16/00* (2006.01)

(52) U.S. Cl.
CPC .... *A61M 16/0666* (2013.01); *A61M 16/0051* (2013.01); *A61M 16/0622* (2014.02); *A61M 16/1005* (2014.02); *A61M 16/201* (2014.02); *A61M 16/0078* (2013.01); *A61M 16/024* (2017.08); *A61M 2016/0027* (2013.01); *A61M 2016/102* (2013.01); *A61M 2230/432* (2013.01)

(58) Field of Classification Search
CPC .......... A61M 16/1005; A61M 16/0672; A61M 16/0666
See application file for complete search history.

(56) References Cited

U.S. PATENT DOCUMENTS 4,823,788 A * 4/1989 Smith ............... A62B 7/04
128/205.24
6,536,432 B2 * 3/2003 Truschel .......... A61M 16/0069
128/202.22

(Continued)

FOREIGN PATENT DOCUMENTS

WO 2016094657 6/2016
WO WO2016159787 A1 10/2016

OTHER PUBLICATIONS

Hayes-Bradley, Clare , et al., "Efficacy of Nasal Cannula Oxygen as a Preoxygenation", vol. 68, Issue 2, Aug. 2016, pp. 174-180.

(Continued)

*Primary Examiner* — LaToya M Louis
(74) *Attorney, Agent, or Firm* — Dentons Durham Jones Pinegar; Sarah W. Matthews

(57) ABSTRACT

A system for detecting manual ventilation and selectively delivering a high flow of oxygen. The system comprises a source of compressed oxygen coupled to a first lumen of a nasal cannula, with an oxygen flow control valve coupled to a processor to control the flow of oxygen to the nasal cannula. A second lumen of the nasal cannula is in connection with a pressure sensor and the pressure sensor in connection with the processor. The processor may receive the pressure values and be programmed to determine when manual ventilation has occurred, and send a signal to the oxygen flow control valve to send a high flow of oxygen in response to manual ventilation.

28 Claims, 10 Drawing Sheets

(56) References Cited

U.S. PATENT DOCUMENTS

| | | | | |
|---|---|---|---|---|
| 6,601,735 B2* | 8/2003 | Milian | ................ | B05B 11/3049 222/402.11 |
| 6,691,896 B2* | 2/2004 | Meshberg | ........... | B05B 11/3059 222/402.11 |
| 2006/0162727 A1* | 7/2006 | Biondi | .............. | A61M 16/0051 128/204.22 |
| 2007/0016093 A1* | 1/2007 | Rapoport | ............ | A61M 16/026 600/533 |
| 2008/0236584 A1* | 10/2008 | Holder | .............. | A61M 16/0672 128/204.23 |
| 2012/0055478 A1 | 3/2012 | Wilkinson | | |
| 2013/0131533 A1* | 5/2013 | Orr | ................... | A61M 16/0616 600/532 |
| 2013/0159912 A1* | 6/2013 | Baker, Jr. | ............ | A61M 16/024 715/772 |
| 2013/0239038 A1* | 9/2013 | Skidmore | .............. | G16H 40/63 715/771 |
| 2015/0120067 A1* | 4/2015 | Wing | ..................... | G05D 16/20 700/282 |
| 2015/0144130 A1* | 5/2015 | O'Donnell | ........ | A61M 16/0051 128/202.22 |
| 2016/0166796 A1* | 6/2016 | Orr | ..................... | A61M 16/201 128/202.22 |
| 2017/0348498 A1* | 12/2017 | Salter | ................... | A61M 16/16 |
| 2018/0085544 A1 | 3/2018 | Holyoake et al. | | |

OTHER PUBLICATIONS

European Patent Office, "Communication under Article 94(3)EPC," European Application No. 19206450.9, dated Oct. 12, 2021.

Extended European Search Report from related European Patent Application No. EP 19206450, dated Mar. 26, 2020.

* cited by examiner

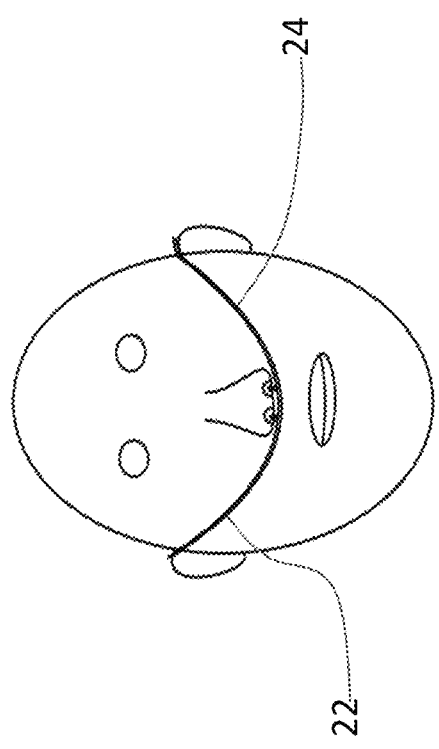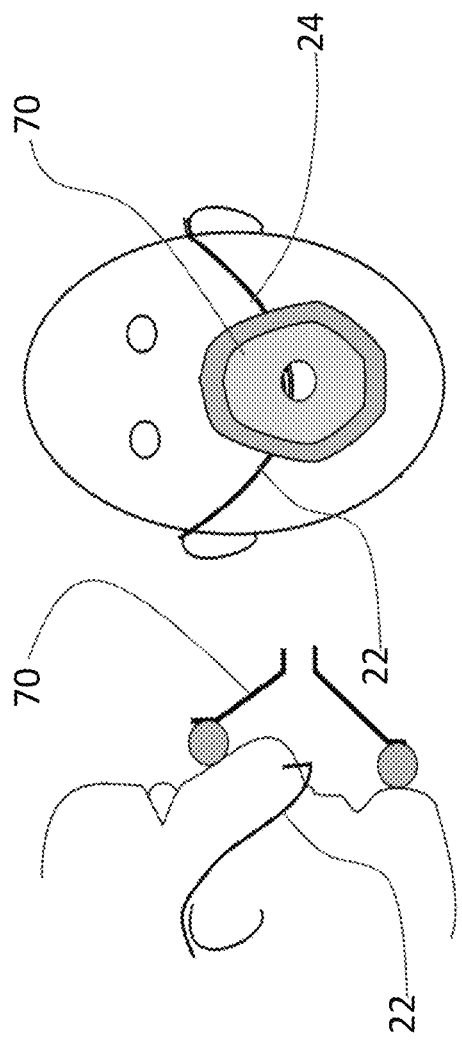

APPARATUS AND METHOD FOR OXYGEN DELIVERY TO A PATIENT DURING MANUAL VENTILATION

TECHNICAL FIELD

The present disclosure relates generally to a system and method to deliver oxygen to a patient under manual, positive pressure ventilation. More specifically, the present disclosure relates to a method and apparatus for detecting manual, positive pressure ventilation, selectively delivering or discontinuing high flow of oxygen, and measuring end-tidal $CO_2$ values.

BACKGROUND

Oxygen is often given via a nasal cannula to patients who exhibit decreased breathing (hypopnea) as a supplement to the oxygen they receive from breathing room air. If the patient stops breathing (apnea), a clinician may need to manually push oxygen into the patient's lungs via positive pressure ventilation using a facemask connected to a reservoir and/or self-inflating bag and/or mechanical ventilator. Clinicians usually remove the nasal cannula prior to placing the mask in order to ensure a relatively leak-proof seal between the face and the mask to optimize lung inflation. Manual, positive pressure lung inflation or ventilation systems often include an oxygen bag-reservoir that collects oxygen while the patient is exhaling and delivers the oxygen to the patient when the bag-reservoir is squeezed to push oxygen into the lungs. Alternatively, the mask is connected to an anesthesia machine that either fills a breathing bag with oxygen before it is squeezed or the anesthesia machine's ventilator inflates the patient's lungs via positive pressure.

Removing the nasal cannula and connecting oxygen to the manual ventilation mask system can interrupt life-sustaining, supplemental oxygen needed by the patient and delays manual breath delivery with the mask. During sedation, this task may need to be repeated often as the patient alternates between spontaneous respiration and apnea. With each iteration, the clinician will need to reacquire an optimal seal between the patient's face and the mask.

Capnometry, or measurement of exhaled $CO_2$ concentration, is often used to monitor the rate and quality of patient breathing. Rate is calculated by measuring the time intervals between elevations in the $CO_2$ signal. The quality of respiration is assessed by evaluating the maximum, or end-tidal $CO_2$ ($etCO_2$) concentration observed during each breath. An $etCO_2$ that is too high can indicate that the patient is, or has been, inadequately ventilated. Alternatively, an $etCO_2$ that is too low could be a sign that breaths are too small to adequately clear the airway dead space. A low $etCO_2$ could also indicate a leak between the face and mask during exhalation thereby decreasing the amount of $etCO_2$ for analysis. When using a nasal cannula for oxygen delivery and $etCO_2$ detection, exhaled $CO_2$ is normally analyzed by continuously drawing a sample of the patient's exhaled breath through a separate lumen of the nasal cannula. In traditional mask ventilation, the nasal cannula is removed before the mask is placed. If the cannula is removed, then the monitoring sample is no longer available during manual ventilation unless the clinician takes the time to disconnect the $CO_2$ sampling line from the nasal cannula and places it on the mask port. If the cannula is left in place during manual ventilation, and oxygen is allowed to flow continuously, the exhaled $CO_2$ sample can be diluted by the oxygen that is constantly flowing through the nasal cannula.

Thus, there is a need to automatically detect when a patient is receiving manual, positive pressure ventilation to augment ventilation when receiving nasal cannula delivered oxygen. This will improve both oxygenation and respiratory monitoring thereby improving safety and possibly patient outcomes by controlling the flow of oxygen to the patient during manual, positive pressure ventilation or otherwise. Secondly, due to the difficulty of removing the cannula and replacing it and subsequent interruption in oxygen delivery to the patient, it may be advantageous for the device to be used with a standard cannula in place. It may also be advantageous for the system to allow an accurate (i.e., undiluted) end-tidal $CO_2$ measurement with the nasal cannula in place.

SUMMARY OF DISCLOSURE

According to one aspect, a system for delivering oxygen to a patient during a manual mask ventilation process may comprise: a nasal cannula comprising a first lumen to convey oxygen from a pressurized oxygen source to the patient's nares, a second lumen, a pressure sensor in communication with the second lumen, the pressure sensor configured to determine an intra-nasal pressure value; an electronic oxygen flow valve in communication with a processor, the oxygen control valve between the pressurized oxygen source and the first lumen of the nasal lumen; a mask to be positioned over the nasal cannula, nose and lips of the patient, the mask for manually delivering oxygen to the patient, the mask configured to, when in place, create a seal between a face of the patient and the mask such that oxygen is routed into lungs of the patient; the processor programmed to receive the intra-nasal pressure value from the pressure sensor in communication with the second lumen; the processor programmed to compare the intra-nasal pressure value to a pre-determined oxygen flow activation threshold pressure value; and the processor programmed to adjust the electronic oxygen flow valve to deliver a pre-determined high oxygen flow through the first lumen when the processor determines the intra-nasal pressure value is greater than the pre-determined lower threshold pressure value.

In some configurations, the pre-determined high oxygen flow may be between about 10 liters to about 30 liters per minute. In some configurations, the pre-determined lower threshold pressure value may be between about 2 cm $H_2O$ and about 5 cm $H_2O$.

According to another aspect, the processor may be further programmed to, after the processor has adjusted the electronic oxygen flow valve to deliver the pre-determined high oxygen flow, compare the intra-nasal pressure value to a pre-determined high pressure threshold value, and the processor programmed to adjust the electronic oxygen flow valve to turn off oxygen flow through the first lumen when the processor determines the intra-nasal pressure value is greater than the pre-determined high pressure threshold value. In some configurations, the pre-determined high pressure threshold value may be between about 12 cm $H_2O$ and about 15 cm $H_2O$.

According to another aspect, the processor may be further programmed to, after the processor has adjusted the electronic oxygen flow valve to deliver the pre-determined high oxygen flow, compare the intra-nasal pressure value to a pre-determined high pressure alarm threshold value and the processor programmed to adjust the electronic oxygen flow valve to turn off all oxygen flow through the first lumen, when the processor determines the intra-nasal pressure value is greater than the pre-determined high pressure alarm threshold value. In some configurations the processor may further activate an alarm when the processor determines the intra-nasal pressure value is greater than the pre-determined high pressure alarm threshold value.

According to another aspect, the processor may be further programmed to, after the processor has adjusted the electronic oxygen flow valve to deliver the pre-determined high oxygen flow through the first lumen, compare the current intra-nasal pressure value to the pre-determined lower threshold pressure value, and wherein the processor is further programmed to adjust the electronic oxygen flow valve to turn off the pre-determined high oxygen flow through the first lumen when the processor determines the intra-nasal pressure value is lower than a pre-determined low pressure threshold.

In some configurations system may further comprise a nasal cannula having a third lumen, and wherein the system further comprises a capnometry device to measure an end-tidal $CO_2$ value, the capnometry device in connection with the third lumen of the nasal cannula, and wherein the processor is further programmed to receive an end-tidal $CO_2$ measurement from the capnometry device after the processor has adjusted the electronic oxygen flow valve to turn off the pre-determined high oxygen flow through the first lumen. The processor may be further programmed to adjust the electronic oxygen flow valve to turn on a pre-determined low oxygen flow through the first lumen after the processor has received the end-tidal $CO_2$ measurement from the capnometry device, the pre-determined low oxygen flow configured to flush exhaled $CO_2$ from the mask. The processor may be further programmed to adjust the electronic oxygen flow valve to turn on the pre-determined low oxygen flow through the first lumen after a pre-determined amount of time for exhalation has passed after the processor adjusted the electronic oxygen flow valve to turn off the pre-determined high oxygen flow through the first lumen. In some configurations, the pre-determined amount of time for exhalation may be about 1 second.

According to another aspect, the processor may be further programmed to, after the processor has adjusted the electronic oxygen flow valve to deliver the pre-determined high oxygen flow through the first lumen, receive, at the processor, an amount of time the electronic oxygen flow valve has delivered the pre-determined high oxygen flow through the first lumen; wherein the processor is programmed to compare the amount of time the electronic oxygen flow valve has delivered the pre-determined high oxygen flow rate through the first lumen with a pre-determined maximum amount of time for high oxygen flow rate delivery; and wherein the processor is programmed to adjust the electronic oxygen flow valve to turn off the pre-determined high oxygen flow through the first lumen when the processor determines the amount of time the electronic oxygen flow valve has delivered the pre-determined high oxygen flow through the first lumen is greater than the pre-determined maximum amount of time for high oxygen flow rate delivery. In some configurations, the pre-determined maximum amount of time for high oxygen flow rate delivery is between 0.5 seconds and 2.5 seconds.

According to another aspect, the processor may be programmed to receive and store a plurality of intra-nasal pressure values over time, and wherein the processor is further programmed to compare each of the plurality of intra-nasal pressures values to the pre-determined lower threshold pressure value to determine a time which a manual ventilation sequence has begun, and wherein the processor is further programmed to receive an amount of time passed since the manual ventilation sequence has begun, and wherein the processor is further programmed to compare the amount of time passed to a predetermined maximum time value, and wherein the processor is further programmed to send an alert to an output device if the amount of time passed is greater than the predetermined maximum time value. The processor may also be further programmed to compare the amount of time passed to a predetermined minimum time value, and wherein the processor is further programmed to send an alert to an output device if the amount of time passes is less than the predetermined minimum time value.

According to another aspect, the processor may be further programmed to receive and store a plurality of intra-nasal pressure values from the pressure sensor to create an intra-nasal pressure log; the processor programmed to analyze each of the plurality of intra-nasal pressure values of the intra-nasal pressure log to determine if a breath has been taken by the patient during a pre-determined amount of time; and the processor further programmed to adjust the electronic oxygen flow valve to deliver the pre-determined high oxygen flow through the first lumen when the processor determines no breath has been taken by the patient during the pre-determined amount of time. In some configurations the pre-determined amount of time is between about 5 seconds and about 30 seconds.

According to another aspect, a system is described for delivering oxygen to a patient, the system comprising: a nasal cannula comprising a first lumen to convey oxygen from a pressurized oxygen source to the patient's nares and a second lumen, a pressure sensor in communication with the second lumen, the pressure sensor configured to determine a pressure between the patient's nares; an electronic oxygen flow valve in communication with a processor, the oxygen control valve between the pressurized oxygen source and the first lumen of the nasal cannula; the processor programmed to receive and store a plurality of intra-nasal pressure values from the pressure sensor to create an intra-nasal pressure log; the processor programmed to analyze each of the plurality of intra-nasal pressure values of the intra-nasal pressure log to determine if a breath has been taken by the patient during a pre-determined amount of time; and the processor further programmed to adjust the electronic oxygen flow valve to deliver a pre-determined high oxygen flow through the first lumen when the processor determines no breath has been taken by the patient during the pre-determined amount of time.

According to another aspect, a method is described for delivering oxygen to a patient during a manual mask ventilation process, the method comprising: positioning a nasal cannula in the patient's nares, the nasal cannula comprising a first lumen to convey oxygen from a pressurized oxygen source to the patient's nares and a second lumen in communication with a pressure sensor configured to determine an intranasal pressure; detecting the patient's intra-nasal pressure value at discrete times to determine a plurality of intranasal pressure values over time, and receiving the plurality of intra-nasal pressure values at at least one processor; the at least one processor analyzing the plurality of intranasal pressure values to determine if manual ventilation is being used, and when the processor determines manual ventilation is being used, the processor communicating with a flow valve to deliver a high-flow pulse of oxygen. The method may further comprise the step of positioning a mask over the nasal cannula, a nose and lips of the patient, the mask for manually delivering oxygen to the patient, the mask configured to, when in place, create a seal between the nose and lips of the patient and the mask such that oxygen is routed into lungs of the patient. The method may further comprise the step of, after the at least one processor determines manual ventilation is being used and the at least one processor communicates with the flow valve to deliver the high-flow pulse of oxygen, the at least one processor comparing the intra-nasal pressure value to a pre-determined high pressure threshold value, and the at least one processor adjusting the flow valve to turn off all oxygen flow through the first lumen when the at least one processor determines the intra-nasal pressure value is greater than the pre-determined high pressure threshold value.

According to another aspect, the second lumen of the system may comprise a high-flow oxygen cannula for connection to a source of high pressure oxygen, and further comprising a pressure sensor in communication with the oxygen cannula, the pressure sensor configured to determine an intra-nasal pressure value.

According to another aspect, the processor may be further programmed to receive and store a plurality of intra-nasal pressure values from the pressure sensor to create an intra-nasal pressure log; the processor programmed to analyze each of the plurality of intra-nasal pressure values of the intra-nasal pressure log to determine the largest positive intra-nasal pressure value measured by the pressure sensor for a breath cycle; and the processor further programmed to adjust the electronic oxygen flow valve to shut off the pre-determined high oxygen flow through the first lumen when the processor determines the intra-nasal pressure value has dropped below the largest positive intra-nasal pressure value. In some configurations, the processor may be further programmed to adjust the electronic oxygen flow valve to shut off the pre-determined high oxygen flow through the first lumen when the processor determines the intra-nasal pressure value has dropped between 1 and 5 cm $H_2O$ below the largest positive intra-nasal pressure value.

According to another aspect, the processor may be further programmed to receive and store a plurality of intra-nasal pressure values from the pressure sensor to create an intra-nasal pressure log; the processor programmed to analyze each of the plurality of intra-nasal pressure values of the intra-nasal pressure log to determine the largest positive intra-nasal pressure value; and the processor further programmed to adjust the electronic oxygen flow valve to shut off the pre-determined high oxygen flow through the first lumen when the processor determines the intra-nasal pressure value has dropped more than 5% lower than the largest positive intra-nasal pressure value.

According to another aspect, a system is described for delivering oxygen to a patient during a manual mask ventilation process, the system comprising: a nasal cannula; means to convey oxygen from a pressurized oxygen source to the patient's nares, a pressure sensor configured to determine an intra-nasal pressure value; an electronic oxygen flow valve in communication with a processor, the oxygen control valve between the pressurized oxygen source and the means to convey oxygen to the patient's nares; a mask to be positioned over the nasal cannula; the processor programmed to receive the intra-nasal pressure value from the pressure sensor; the processor programmed to compare the intra-nasal pressure value to a pre-determined oxygen flow activation threshold pressure value; and the processor programmed to adjust the electronic oxygen flow valve to deliver a pre-determined high oxygen flow through the means to convey oxygen from the pressurized oxygen source to the patient's nares when the processor determines the intra-nasal pressure value is greater than the pre-determined lower threshold pressure value.

BRIEF DESCRIPTION OF DRAWINGS

The following drawings illustrate what are currently considered to be specific representative configurations for carrying out the invention and are not limiting as to embodiments which may be made in accordance with the present invention. The components in the drawings are not necessarily to scale relative to each other. Like reference numerals designate corresponding parts throughout the several views.

The drawings are illustrative and not limiting of the scope of the invention which is defined by the appended claims. The various elements of the invention accomplish various aspects and objects of the invention. Not every element of the invention can be clearly displayed in a single drawing, and as such not every drawing shows each element of the invention.

FIG. 2 is a front view of a patient with a nasal cannula in place.

FIG. 3 is a side view of a patient with a nasal cannula and mask in place.

FIG. 4 is a front view of the patient of FIG. 3 with a nasal cannula and mask in place.

DETAILED DESCRIPTION

Figure 1:
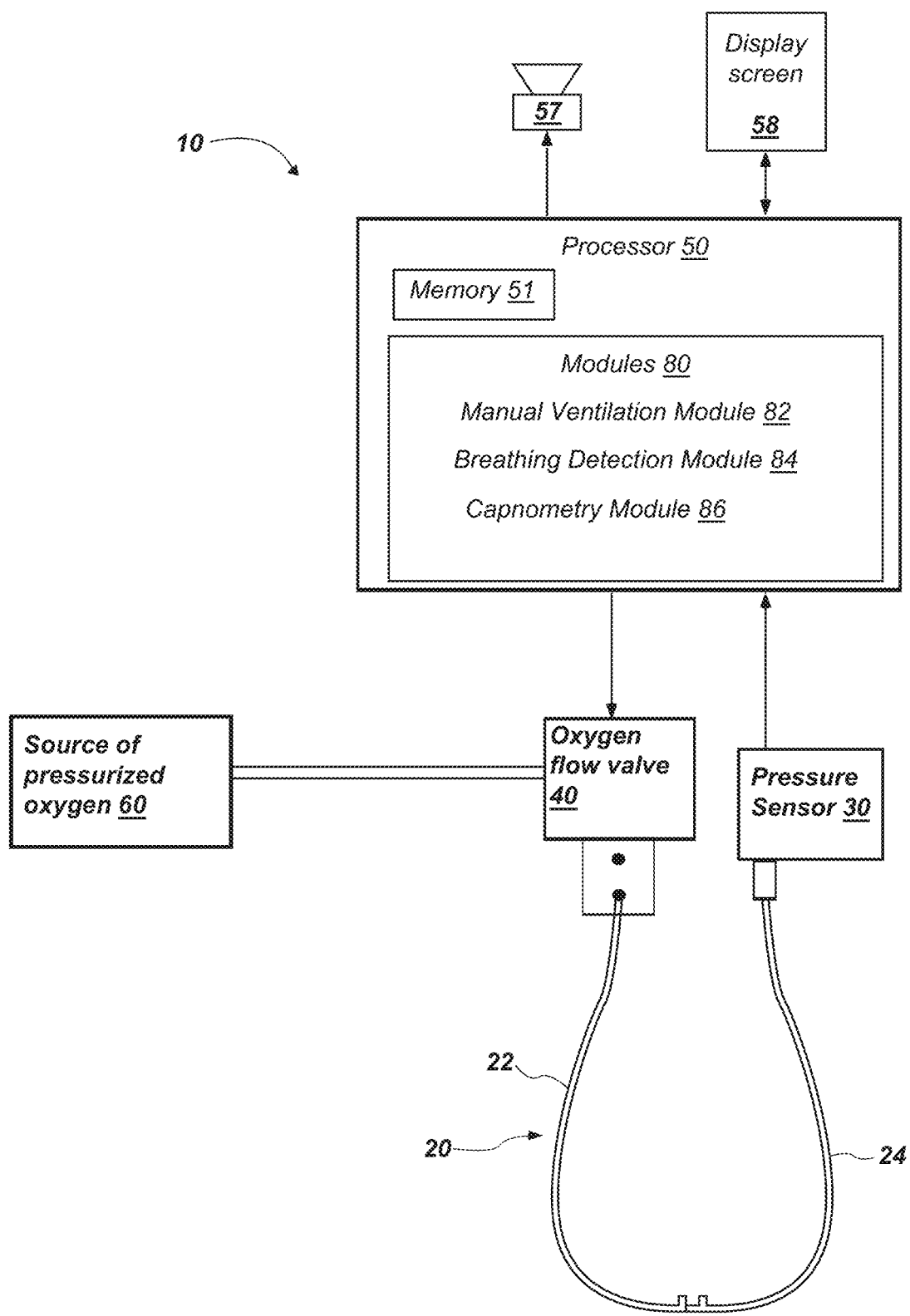
FIG. 1 is a block diagram of a system to deliver oxygen to a patient.

The following provides a detailed description of particular embodiments of the present invention. Reference will now be made to the drawings in which the various elements of the illustrated configurations will be given numerical designations and in which the invention will be discussed so as to enable one skilled in the art to make and use the invention. It is to be understood that the following description is only exemplary of the principles of the present invention, and should not be viewed as narrowing the scope of the claims which follow, which claims define the full scope of the invention.

It will be appreciated that various aspects discussed in one drawing may be present and/or used in conjunction with the embodiment shown in another drawing, and each element shown in multiple drawings may be discussed only once. For example, in some cases, detailed description of well-known items or repeated description of substantially the same configurations may be omitted. This facilitates the understanding of those skilled in the art by avoiding an unnecessarily redundant description. The accompanying drawings and the following description are provided in order for those skilled in the art to fully understand the present disclosure, and these are not intended to limit the gist disclosed in the scope of claims.

It should be noted that the description merely illustrates the principles of the present subject matter. It will thus be appreciated that those skilled in the art will be able to devise various arrangements that, although not explicitly described herein, embody the principles of the present subject matter and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

Reference in the specification to "one configuration" "one embodiment," "a configuration" or "an embodiment" means that a particular feature, structure, or characteristic described in connection with the configuration is included in at least one configuration, but is not a requirement that such feature, structure or characteristic be present in any particular configuration unless expressly set forth in the claims as being present. The appearances of the phrase "in one configuration" in various places may not necessarily limit the inclusion of a particular element of the invention to a single configuration, rather the element may be included in other or all configurations discussed herein.

Furthermore, the described features, structures, or characteristics of configurations of the invention may be combined in any suitable manner in one or more configurations. In the following description, numerous specific details are provided, such as examples of products or manufacturing techniques that may be used, to provide a thorough understanding of configurations of the invention. One skilled in the relevant art will recognize, however, that configurations of the invention may be practiced without one or more of the specific details, or with other methods, components, materials, and so forth. In other instances, well-known structures, materials, or operations are not shown or described in detail to avoid obscuring aspects of the invention.

Before the present invention is disclosed and described in detail, it should be understood that the present disclosure is not limited to any particular structures, process steps, or materials discussed or disclosed herein, but is extended to include equivalents thereof as would be recognized by those of ordinary skill in the relevant art. More specifically, the invention is defined by the terms set forth in the claims. It should also be understood that terminology contained herein is used for the purpose of describing particular aspects of the invention only and is not intended to limit the invention to the aspects or configurations shown unless expressly indicated as such. Likewise, the discussion of any particular aspect of the invention is not to be understood as a requirement that such aspect is required to be present apart from an express inclusion of the aspect in the claims.

It should also be noted that, as used in this specification and the appended claims, singular forms such as "a," "an," and "the" may include the plural unless the context clearly dictates otherwise. Thus, for example, reference to "a micro controller" may include one or more of such microcontrollers, and reference to "the sensor" may include reference to one or more of such sensors.

As used herein, the term "substantially" refers to the complete or nearly complete extent or degree of an action, characteristic, property, state, structure, item, or result to function as indicated. For example, an object, such as a sensor, that is "substantially" enclosed would mean that the object is either completely enclosed or nearly completely enclosed. The use of "substantially" is equally applicable when used in a negative connotation to refer to the complete or near complete lack of an action, characteristic, property, state, structure, item, or result. For example, a mask which "substantially" forms a seal with a patient's face would either completely form a seal or so nearly completely form a seal that the effect would be effectively the same as if it did form the seal.

As used herein the term "generally" refers to something that is more of the designated adjective than not, or the converse if used in the negative.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

For a firmware, and/or software implementation, the methodologies to analyze breathing pressure values can be implemented with modules (e.g., procedures, functions, and so on) that perform the functions described herein. Any machine readable medium tangibly embodying instructions can be used in implementing the methodologies described herein. For example, software codes and programs can be stored in a memory and executed by a processing unit. Memory can be implemented within the processing unit or may be external to the processing unit. As used herein the term "memory" refers to any type of long term, short term, volatile, nonvolatile, or other storage devices and is not to be limited to any particular type of memory or number of memories, or type of media upon which memory is stored.

In another firmware and/or software implementation, the functions may be stored as one or more instructions or code on a non-transitory computer-readable medium. Examples include computer-readable media encoded with a data structure and computer-readable media encoded with a computer program. Computer-readable media may take the form of an article of manufacturer. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store reproduce data magnetically, while discs reproduce data optically with lasers. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims. That is, the communication apparatus includes transmission media with signals indicative of information to perform disclosed functions. At a first time, the transmission media included in the communication apparatus may include a first portion of the information to perform the disclosed functions, while at a second time the transmission media included in the communication apparatus may include a second portion of the information to perform the disclosed functions.

It should be noted that the description merely illustrates the principles of the present subject matter. It will thus be appreciated that those skilled in the art will be able to devise various arrangements that, although not explicitly described herein, embody the principles of the present subject matter and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

The manner in which the systems and methods may be implemented is explained in details with respect to the figures. While aspects of described systems and methods can be implemented in any number of different computing systems, transmission environments, and/or configurations, the embodiments are described in the context of the following exemplary system(s).

It will also be appreciated by those skilled in the art that the words during, while, and when as used herein are not exact terms that mean an action takes place instantly upon an initiating action but that there may be some small but reasonable delay, such as a propagation delay, between the initial action and the reaction that is initiated by the initial action. Additionally, the word "connected" and "coupled" is used throughout for clarity of the description and can include either a direct connection or an indirect connection.

The present disclosure relates generally to a system and method for delivering a high flow of oxygen to a patient during manual ventilation. One particular embodiment of the present disclosure is shown and described in the system of FIG. 1. FIG. 1 is a block diagram of a system to deliver oxygen according to one aspect of this disclosure. The system 10 may consist generally of a nasal cannula 20, one or more pressure sensors 30, an oxygen flow valve 40 in communication with a processor or micro-controller 50 and a source of pressurized oxygen 60, and a mask 70 to be positioned over the patient's nose and mouth.

The nasal cannula 20 may have one or more cannulas or lumens. In some configurations, a single cannula with three lumens may be used. In other variations, one or more separate cannulas may be used. It will be appreciated that while many examples are given herein of a single cannula with a plurality of lumens, an equivalently functioning system could be comprised of a plurality of separate cannulas. In one aspect, the nasal cannula 20 has a first lumen 22 to convey oxygen from the source of pressurized oxygen 60 to the patient's nares. An oxygen control flow valve 40 may be located between the source of pressurized oxygen 60 and the first lumen 22. The oxygen flow valve 40 may also be in communication, either directly or wirelessly, with a processor 50 to control the flow of oxygen from the pressurized oxygen source 60 to the first lumen 22 of the nasal cannula 20. The oxygen flow valve may include any suitable valve which may be controlled by a processor or controller 50, such as a fixed or variable flow (proportional) valve to control the flow of oxygen between the oxygen source 60 and the first lumen 22 of the nasal cannula. It may be an electronic flow valve, solenoid, proportional valve, etc.

The nasal cannula may also have a second lumen 24, and the pressure sensor or pressure transducer 30 may be located in or proximal to the second lumen 24 such that the pressure value in the patient's nares may be measured by the pressure sensor 30 at a given time. As used here, the term "intranasal pressure" is used to refer to the pressure value read by the pressure sensor 30. The term "intranasal pressure" therefore encompasses not only the intranasal pressure at certain times, but may also encompass other pressure readings if the nasal cannula becomes dislodged. For example, it may encompass the mask pressure in the case where the nasal cannula becomes dislodged and a mask is in place over the cannula. In some configurations, the pressure value in the patient's nares or otherwise measured by pressure sensor 30 may be measured continually or substantially continually. In other configurations, the pressure value may be measured at pre-determined time intervals. The pressure sensor 30 may be in connection, either directly or wirelessly, with the processor 50 such that the processor may receive pressure values measured by the pressure sensor 30 in the second lumen 24. The processor may store such pressure values received from the pressure sensor 30 on memory 51, including storing the pressure values and their corresponding time values such that the pressure values may be analyzed over time. The nasal cannula may also be provided with a third lumen 26 in some configurations, the third lumen 26 housing an end-tidal $CO_2$ measurement device as discussed in more detail below. In other configurations, fewer than three cannulas or three lumens of a single cannula may be used. For example, in a configuration where the high flow of oxygen is shut off after a set time, the pressure sensor could be connected to the oxygen line and a single lumen cannula could be used.

FIGS. 2-4 illustrate a mask 70 which may be provided to be placed over the patient's nose and mouth, as well as the nasal cannula. Typically, medical personnel remove the nasal cannula each time they perform manual ventilation of a patient. However, nasal cannulas may be somewhat difficult to remove and replace. According to one aspect, the nasal cannula may remain in place and the mask for manual ventilation may be placed over the patient's nose and mouth. Masks typically have a cushion 72 around the perimeter that contacts the face of the patient, around the patient's nose and mouth. Such cushion 72 may help to improve the seal of the mask over the nasal cannula.

The mask may be placed by the clinician at the start of manual positive pressure ventilation, and attached to a manual ventilation bag (for clarity, ventilation bag not shown in FIGS. 2-4). With the mask and manual ventilation back in place, oxygen delivered to the patient through the nasal cannula may be directed or routed into the lungs of the patient (as opposed to the ambient air).

The processor 50 may include memory 51, and one or more modules 80. The modules 80 may be programmed to allow the processor 50 to execute one or more functions. During normal operation, the system 10 may essentially function as an oxygen conserving device as is known in the art, and may be programmed to deliver oxygen flow as the patient is inhaling as identified by negative intranasal pressure.

In one implementation, a manual ventilation module 82 may be used by the processor to determine when manual ventilation is occurring and to take specific actions in response to detected manual ventilation. For example, the processor may be programmed with a predetermined oxygen flow activation threshold pressure value. Detection of this predetermined oxygen flow activation threshold pressure value by the processor may trigger the system 10 to deliver a high flow of oxygen to the patient in response. For example, when a patient is not receiving manual positive pressure ventilation, pressure values measured by the pressure sensor 30 and received at the processor 50 are typically less than about 2 cm $H_2O$. In some cases with a mask in place and a good seal, the pressure values may be slightly higher. However, when a clinician places a mask over the cannula 20 and begins manual ventilation, much higher-pressure values are measured at the patient's nares by pressure sensor 30. An oxygen flow activation threshold pressure value may thus be about 2 cm $H_2O$. As the processor receives pressure values from the pressure sensor 30, the processor may continuously or substantially continuously query whether the pressure value is equal to or greater than the pre-programmed oxygen flow activation threshold pressure value. A clinician may also program the processor 50 with a unique oxygen flow activation threshold pressure value for the particular patient, including based on the patient's own breathing patterns, seal of the mask for the particular patient, etc.

If the processor 50 determines the pressure value is equal to or greater than the pre-programmed oxygen flow activation threshold pressure value, the processor 50 may then send a signal to oxygen flow valve 40 to deliver a high flow of oxygen to the patient. When a pressure that is greater than what would be expected during normal spontaneous breathing is detected, the algorithm in the processor 50 assumes that manual positive pressure ventilation is occurring and activates the oxygen control valve to deliver oxygen as the lungs are being pressurized. The high flow of oxygen may be a pre-determined high flow of oxygen (such as, for example, about 10 L/min to about 30 L/min), or it may be adjusted for the particular patient's needs. This high oxygen flow supplements the delivery of oxygen for better alveolar ventilation and assists in pressurizing the mask.

The processor 50 may be further programmed to take an action when an upper threshold, or pre-determined high threshold pressure value is reached after a high flow of oxygen has been delivered. This may prevent the pressure in the mask from becoming too high which may increase the risk of emesis and/or passive gastro-esophageal reflux. In this configuration, the processor 50 may first determine that manual mask ventilation is occurring, as evidenced by pressure values received at the processor 50 from the pressure sensor 30 which are equal to or greater than the predetermined oxygen flow activation threshold pressure value. Then, if the pressure inside the mask 70, as measured by pressure sensor 30 reaches the pre-determined high threshold pressure value, the processor may adjust the electronic oxygen flow valve 40 to turn off all oxygen flow through the first lumen of the cannula 22. This feature may provide the advantage of reducing the risk of emesis and/or passive reflux which can cause aspiration of stomach contents, and may protect the lungs from excessively high pressures. The predetermined high pressure threshold value may be, for example, between about 12 cm $H_2O$ and about 15 cm $H_2O$.

The system 10 may have a further alarm if a higher pressure is reached, above the predetermined high threshold pressure value. Alarms, including visual alarms on a display screen 58 and/or audible alarms through a speaker 57 may also be set to alert when the processor 50 determines the pressure is above a safe level. The alarm threshold pressure and the pressure at which oxygen flow is turned off may be at different levels, the alarm level typically being greater than the oxygen turn off level. In some configurations, the display screen 58 may be set to automatically display a pressure gauge indicating the real-time pressure within the mask 70, when the processor determines manual ventilation is occurring. A clinician may use the pressure gauge on the display screen 58 to guide the manual ventilation.

The processor 50 may be further programmed to take an action when a lower threshold, or pre-determined lower threshold pressure value is reached after a high flow of oxygen has been delivered. This may allow the system to ensure that it does not deliver the high oxygen flow again until a low pressure has been detected indicating the patient has sufficiently exhaled and a new breath is anticipated. In this configuration, the processor 50 may first determine that manual mask ventilation is occurring, as evidenced by pressure values received at the processor 50 from the pressure sensor 30 which are equal to or greater than the pre-programmed oxygen flow activation threshold pressure value. Then, if the pressure inside the mask 70, as measured by pressure sensor 30 drops to the predetermined lower threshold pressure value, the processor may adjust the electronic oxygen flow valve 40 to turn off all oxygen flow through the first lumen 22. The predetermined lower pressure threshold value may be between about 1 cm $H_2O$ and about 2 cm $H_2O$. The lower pressure threshold value may also be determined dynamically as some fixed level below the maximum pressure observed during the breath.

In other configurations, the system may be pre-programmed to deliver the high oxygen flow for a specific amount of time. The system may also be pre-programmed with a maximum amount of time to deliver the high oxygen flow. In still other configurations, the system may be configured to deliver the high oxygen flow until one of the following occurs: (1) the pressure, as measured by the pressure sensor 30, reaches a predetermined upper pressure threshold value; (2) the pressure, as measured by the pressure sensor 30, drops to a predetermined lower pressure threshold value; (3) a maximum amount of time for high oxygen flow rate delivery is reached. The pre-determined maximum amount of time for high oxygen flow rate delivery may be about 0.75 seconds to about 2.0 seconds. The predetermined maximum amount of time for high oxygen flow rate delivery may be set for a patient depending on their unique needs.

The system 10 may further comprise alarms, such as audible alarms through audio output devices 57, visual alarms presented on a display screen 58, or both audible and visual alarms. Such alarms may be triggered by unsafe pressures within the mask 70, the failure of the patient to take a breath in a predetermined time period, etc.

According to another aspect, the system may be provided with a nasal cannula having a third lumen, and a capnometry device to measure an end-tidal $CO_2$ value. A capnometry module 68 may be provided to assist the processor in executing one or more of the following functions. The processor may first determine if the patient is exhaling or inhaling via the pressure sensor 30 in the second lumen of the cannula 24. If the patient is breathing spontaneously while the mask is in place on the patient's face, inhalation is detected as negative (less than ambient) pressure by the pressure sensor 30 in communication with the second lumen of the cannula 24 (FIG. 1), while exhalation is detected as a positive pressure. The processor may be programmed to adjust the electronic oxygen flow valve to turn off any oxygen flow through the first lumen 22 (FIG. 1) when it determines the patient is exhaling (positive pressure), and then receive the end-tidal $CO_2$ value. This may prevent any oxygen flow through the first lumen 22 of the nasal cannula 20 from diluting or otherwise obscuring the end-tidal $CO_2$ value. Because oxygen is turned off when the patient exhales, there is less distortion of the end-tidal $CO_2$ measurement due to the diluting effects of the oxygen.

After the oxygen flow has been turned off and the end-tidal $CO_2$ value received by the processor 50, the processor 50 may then be programmed to automatically initiate a predetermined low oxygen flow through the first lumen 22. This predetermined low oxygen flow may assist in flushing the patient's exhaled $CO_2$ from the mask. According to another configuration, the processor 50 may be programmed to automatically adjust the electronic oxygen flow valve 40 to turn on the pre-determined low oxygen flow through the first lumen 22 after a pre-determined amount of time for exhalation has passed, after the processor adjusted the electronic oxygen flow valve to turn off the pre-determined high oxygen flow through the first lumen 22 for the end-tidal $CO_2$ measurement. The pre-determined amount of time for exhalation may be for example, about 0.75 seconds to about 2.0 seconds and may be set by a clinician to a unique value for a particular patient.

The system may also be programmed to create a log of the intra-nasal pressures, as measured by pressure sensor 30, over time. By creating a log of the pressures over time, the processor may analyze the various pressures to determine when the patient is inhaling, exhaling, receiving manual ventilation, etc. For example, the processor may take one or more of the following steps: (1) compare each of the plurality of intra-nasal pressures values to the pre-determined lower threshold pressure value to determine a time which a manual ventilation sequence has begun; (2) receive an amount of time passed since the manual ventilation sequence has begun; (3) compare the amount of time passed to a predetermined maximum time value; (4) send an alert to an output device if the amount of time passed is greater than the predetermined maximum time value; (5) turn off the high flow of oxygen if the amount of time passed is greater than the predetermined maximum time value.

In other configurations, the processor may compare the amount of time passed to a predetermined minimum time value, and send an alert to an output device if the amount of time passed is less than the predetermined minimum time value.

The system may also take other steps to ensure the safety of a patient. For example, the processor may be provided with a breathing detection module 84, such that the processor may analyze each of the plurality of intra-nasal pressure values of the pressure log to determine if a breath has been taken during a pre-determined time frame. By analyzing pressures over time, the processor may detect an event where the clinician fails to give a manual breath during a predetermined time. This situation may occur when the clinician is distracted with other patient-care tasks such that he or she neglects to pressurize the patient mask to insufflate the patient's lungs. The processor may be programmed to adjust the electronic oxygen flow valve to deliver the pre-determined high oxygen flow through the first lumen 22 when the processor determines no breath has been taken by the patient. The high oxygen flow may raise intra-mask pressure to a level that will force a volume gas into the patient's lungs.

In some configurations, the pre-determined amount of time to determine if a breath has been taken comprises about 5 seconds to about 30 seconds, and it is anticipated that the clinician may be able to set a specialized value for the patient depending on their needs. Alarms, including visual alarms on a display screen 58 and/or audible alarms through a speaker 57 may also be set to alert when the processor 50 determines the patient has not taken a breath in the predetermined time frame, and/or has not taken a sufficient number of breaths, and/or has taken too shallow of breaths.

In use, the method for delivering oxygen to a patient during manual mask ventilation may comprise the step of first positioning the nasal cannula 20 in, or near, the patient's nares. A first lumen 22 of the cannula 20 to convey oxygen from a pressurized oxygen source to the patient's nares may be placed, as well as a second lumen 24 of the cannula 20 in communication with a pressure sensor 30, such that the pressure sensor 30 may determine an intranasal pressure of the patient. A processor 50 may be connected to the oxygen flow valve 40 to control the flow of oxygen from a source of pressurized oxygen 60, and also to the pressure sensor 30 to receive intranasal pressure values from the pressure sensor 30. If it is desired to take end tidal $CO_2$ values, a third lumen 26 may be placed, having a capnometry device connected thereto.

The clinician may either set custom parameters for the patient (for example, by using an input device and/or display screen 58) or may not set custom parameters and instead use default parameters. Custom parameters may include the pre-determined oxygen flow activation threshold pressure value (i.e., the pressure at which the system determines manual ventilation is occurring), the pre-determined high oxygen flow rate (typically in liters per minute), a pre-determined high pressure threshold value, pre-determined high pressure alarm threshold value, a predetermined low pressure threshold, a pre-determined amount of time for exhalation, a predetermined maximum amount of time for high oxygen flow rate delivery, a predetermined timeframe in which a breath may be detected, a value below the largest positive nasal pressure value to turn off the high oxygen flow, a percentage of the largest positive nasal pressure value to turn off the high oxygen flow, etc. The clinician may customize some parameters for the particular patient and select the default settings for other parameters.

When the clinician determines the patient is in need of manual ventilation (either because the clinician has determined themselves the patient is not sufficiently breathing or because system 10 has alerted the clinician the patient is not sufficiently breathing), the clinician may place mask 70 over the nasal cannula 20 and over the patient's nose and mouth. The cushion 72 may generally contact the skin of the patient around the nose and mouth and form a seal. The clinician may then place a bag for manual ventilation in contact with the mask and perform manual ventilation. In other configurations, the clinician may connect the mask to the breathing circuit of an anesthesia machine and perform manual ventilation using the manual ventilation bag that is connected to the anesthesia machine.

The system 10 will continue to send the detected intra-nasal pressures from the pressure sensor 30 to the processor 50. As the processor continuously analyzes the intranasal pressures received, upon manual ventilation it will detect a pressure above the pre-determined oxygen flow activation threshold pressure value. In response, the processor 50 will send a signal to the oxygen flow valve 40 to open the valve and deliver the pre-determined high oxygen flow through the first lumen 22. This high oxygen flow may be delivered for a pre-determined maximum amount of time, or it may be delivered until a predetermined high pressure threshold value is reached or until the pressure drops to a predetermined low pressure threshold value.

Turning now to FIGS. 5-8, there is shown exemplary logic which may be employed by processor 50, executing instructions according to one or more modules 80, such as a manual ventilation module 80, breathing detection module 84, capnometry module, and/or other modules.

Figure 5:
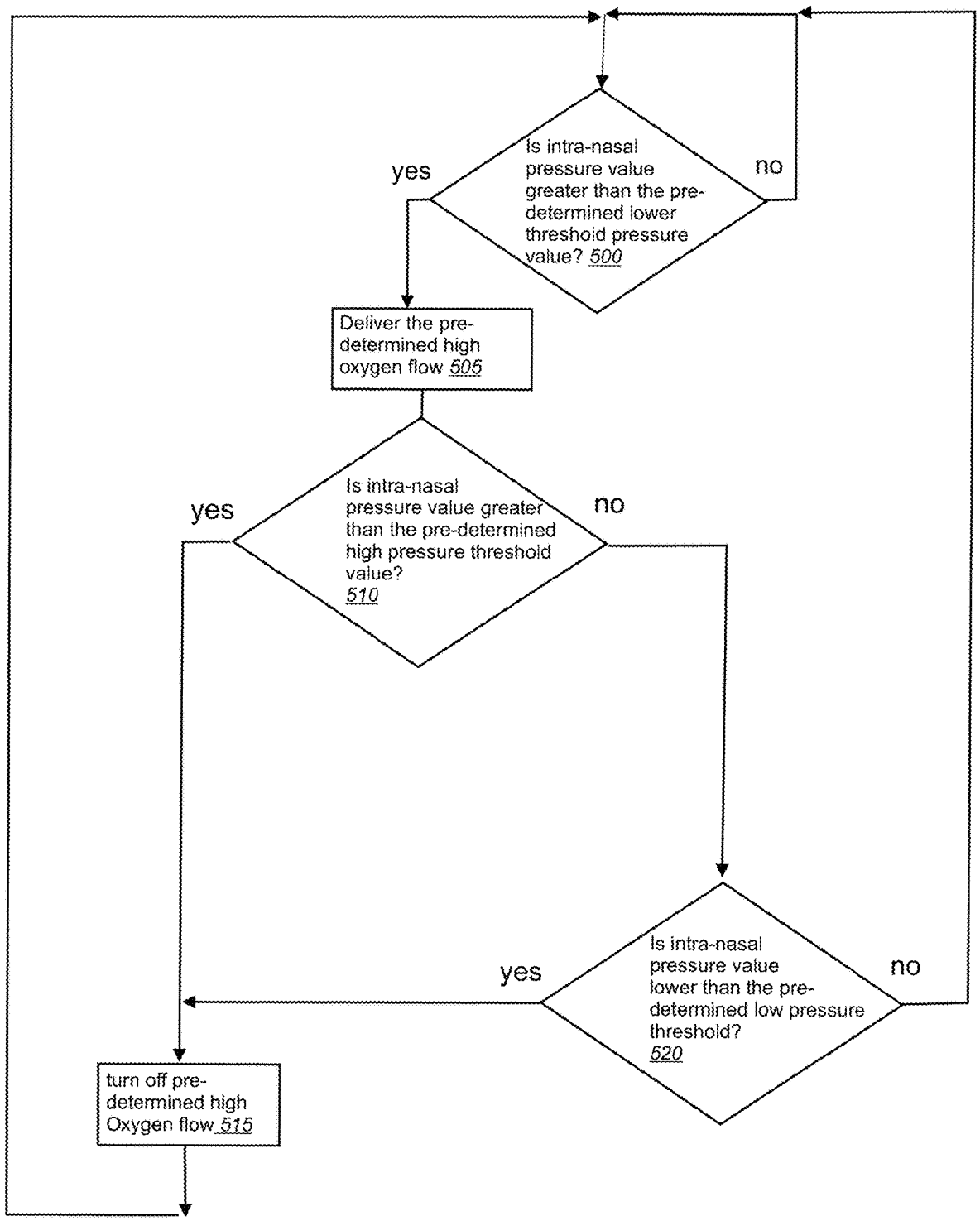
FIG. 5 shows exemplary logic which may be performed by one or more processors of the present system.
Figure 6:
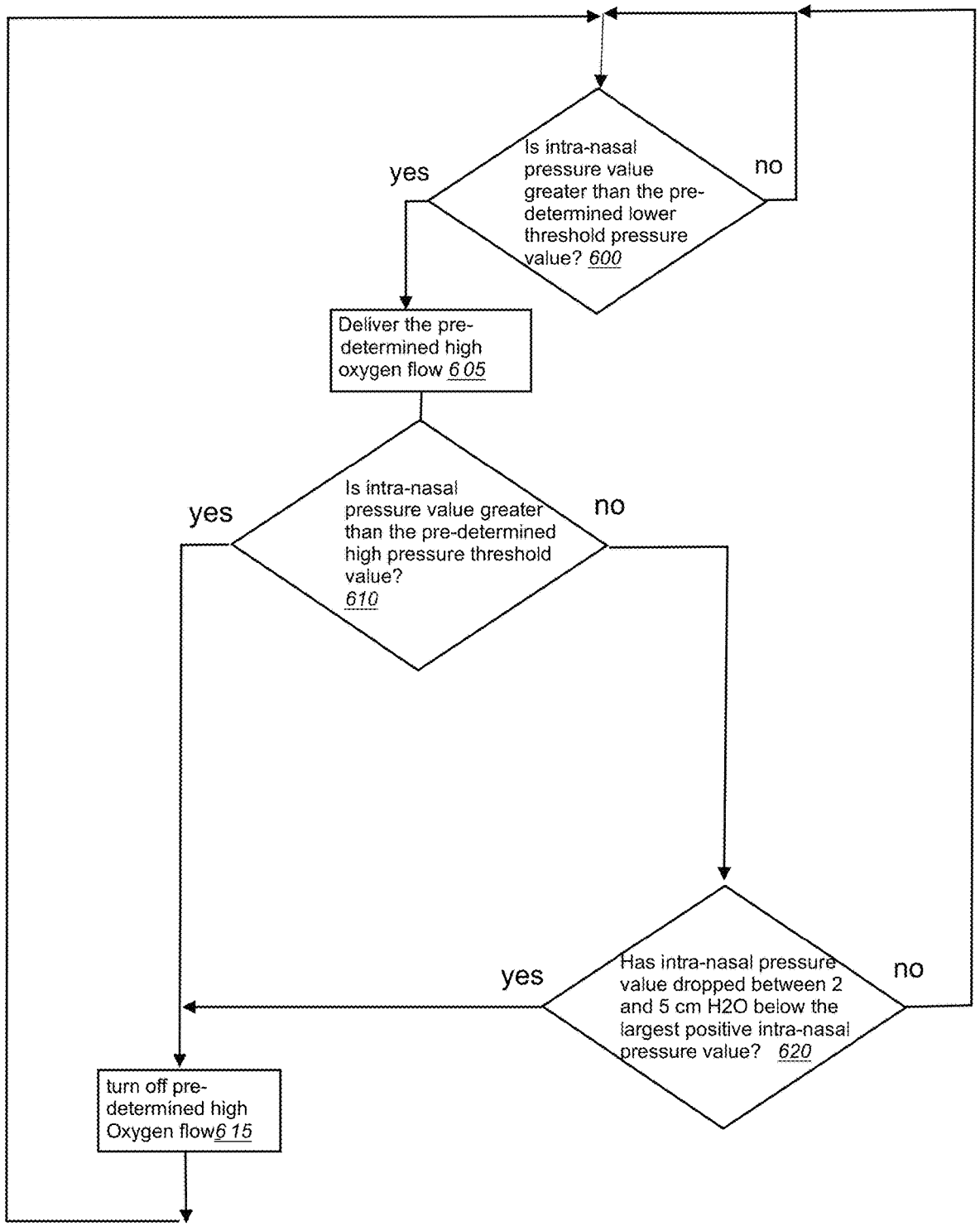
FIG. 6 shows exemplary logic which may be performed by one or more processors of the present system.

According to FIG. 5, the system may continuously or nearly continuously receive a current intra-nasal pressure value as detected by the pressure sensor 30 in communication with the lumen 24. The system may query for each intra-nasal pressure value to determine if the intra-nasal pressure value is greater than the pre-determined lower threshold pressure value (500). If not greater, the system continues to receive the intra-nasal pressure values and query. If the intra-nasal pressure value is greater than the pre-determined lower threshold pressure value, the system assumes a mask is in place and manual ventilation is occurring. In response the system delivers oxygen as the lungs are being pressurized; the system delivers the pre-determined high oxygen flow (505). After the high oxygen flow has been turned on, the system continues to receive intra-nasal pressure values and query to determine if the intra-nasal pressure values are greater than the pre-determined high pressure threshold value (510). If greater than the high pressure threshold value, there is no need to deliver the high flow and doing so could pose a risk to the patient. In response to an intra-nasal pressure value greater than the pre-determined high pressure threshold value, the system may turn off the pre-determined high oxygen flow for safety (515). The system may re-start after it is determined that the patient is having regular breaths, typically in the range of −2 cm $H_2O$ to +2 cm $H_2O$. The system may query to determine if the intra-nasal pressure value is lower than the pre-determined low pressure threshold (520), i.e., in the normal expected range for regular breaths, and start the process again when it determines the intra-nasal pressure value is lower than the pre-determined low pressure threshold.

In other configurations, rather than query to determine if the intra-nasal pressure value is lower than the pre-determined low pressure threshold, the system may determine the largest positive intra-nasal pressure value for a breath cycle (i.e., the peak of the inhalation). The system may then query to determine if the intra-nasal pressure value reached a value between 1 and 5 cm $H_2O$ below the largest positive intra-nasal pressure value (620 in FIG. 6), and shut off the pre-determined high flow of oxygen in response to a drop in pressure (615). This may allow the system to take an accurate end-tidal $CO_2$ measurement without having to wait for the intra-nasal pressure to drop below the pre-determined low pressure threshold. In a similar manner, the system may also query to determine if the intra-nasal pressure value has dropped a certain percentage below the largest positive intra-nasal pressure value. For example, the system may automatically shut-off the high flow of oxygen if the intra-nasal pressure has decreased 5% below the largest positive intra-nasal pressure value, or 20%, etc.

Figure 7:
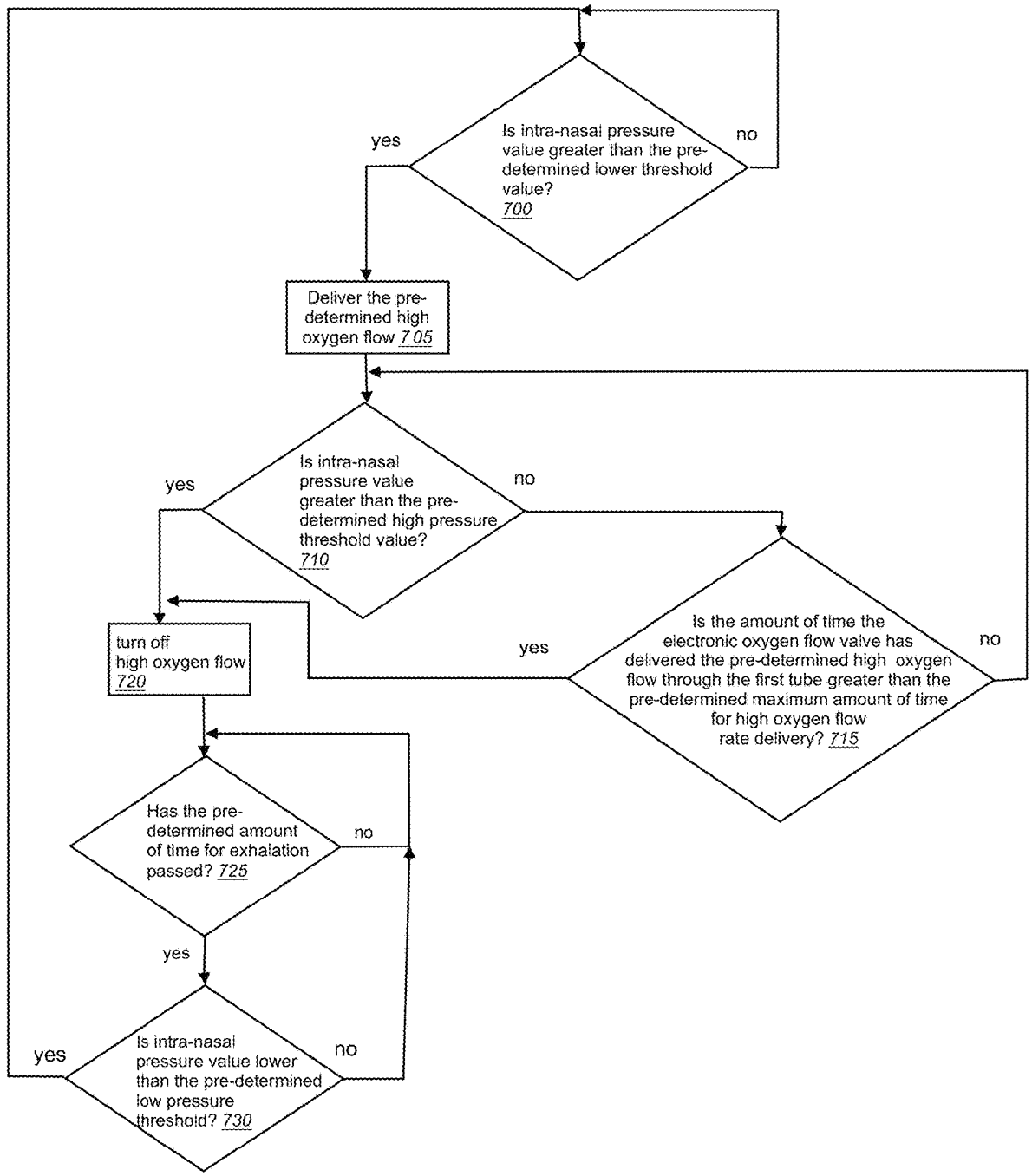
FIG. 7 shows exemplary logic which may be performed by one or more processors of the present system.

As seen in FIG. 7, the system may also shut-down the high flow of oxygen in response to a specific time limit for high flow of oxygen. The system may proceed similarly as described in FIGS. 5-6 above to turn on high oxygen flow (705) in response to an intra-nasal pressure value greater than the pre-determined lower threshold pressure value (700). The system may then query to determine if the amount of time the electronic oxygen flow valve has delivered the pre-determined high oxygen flow through the first lumen 22 greater than the pre-determined maximum amount of time for high oxygen flow rate delivery (715). Where the time is equal to or greater than the pre-determined maximum amount of time for high oxygen flow rate delivery, the system may turn off high oxygen flow (720). The system may re-set, or may optionally query to determine if a pre-determined amount of time for exhalation passed (725) and if the intra-nasal pressure is lower than the pre-determined low pressure threshold (730).

Figure 8:
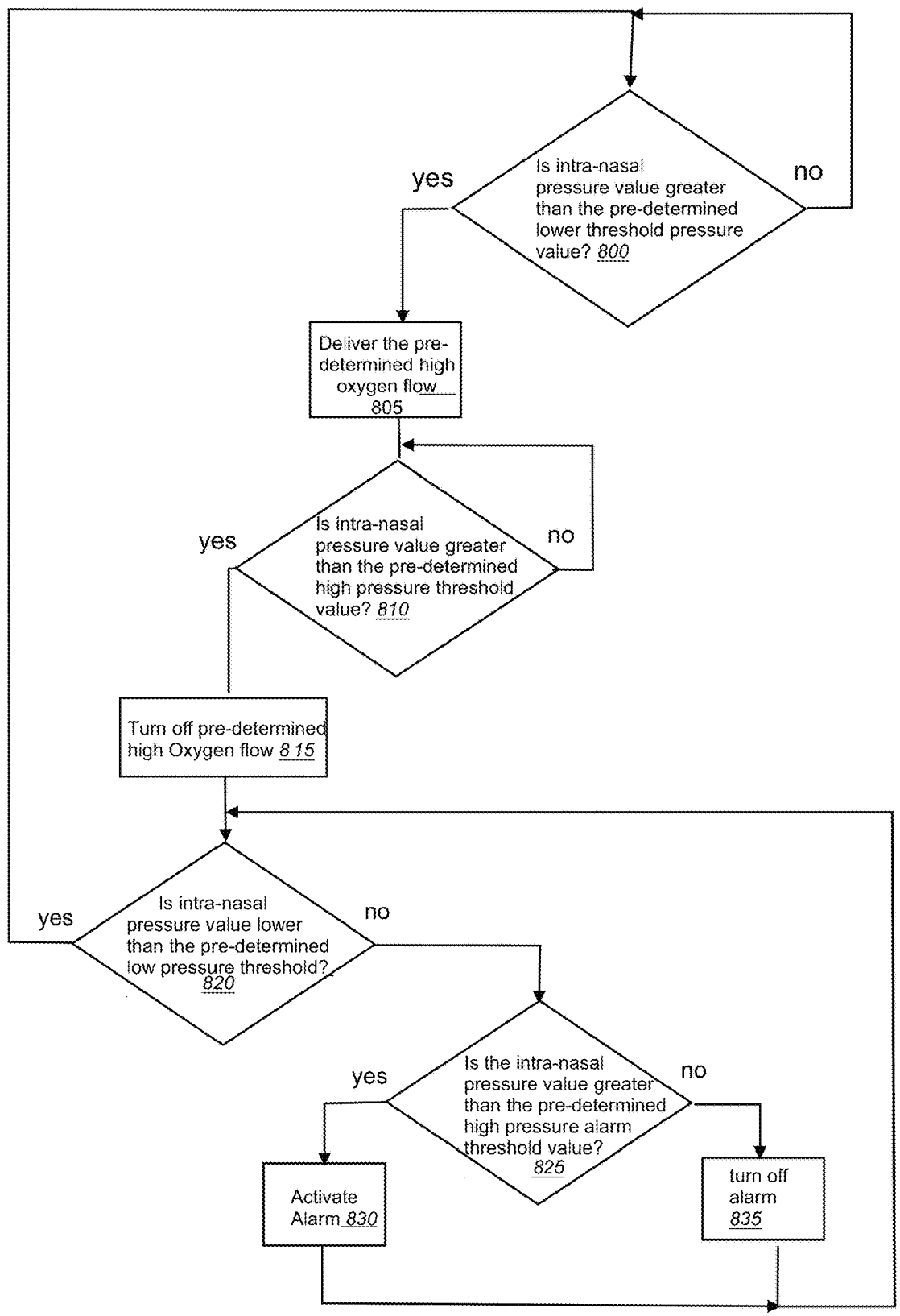
FIG. 8 shows exemplary logic which may be performed by one or more processors of the present system.

FIG. 8 shows an exemplary logic where the processor may further consider if the intra-nasal pressure is greater than a predetermined high pressure alarm threshold value (825). This value is typically slightly greater than the pre-determined high pressure threshold value, and in response to the danger this elevated pressure poses, the processor may activate an alarm (830).

It will be appreciated that while FIGS. 5-8 illustrate specific processes taken in discrete steps, one or more of the steps may be taken at the same time and the order presented may be changed. Additionally, the processor may run multiple processes at the same time.

Figure 10:
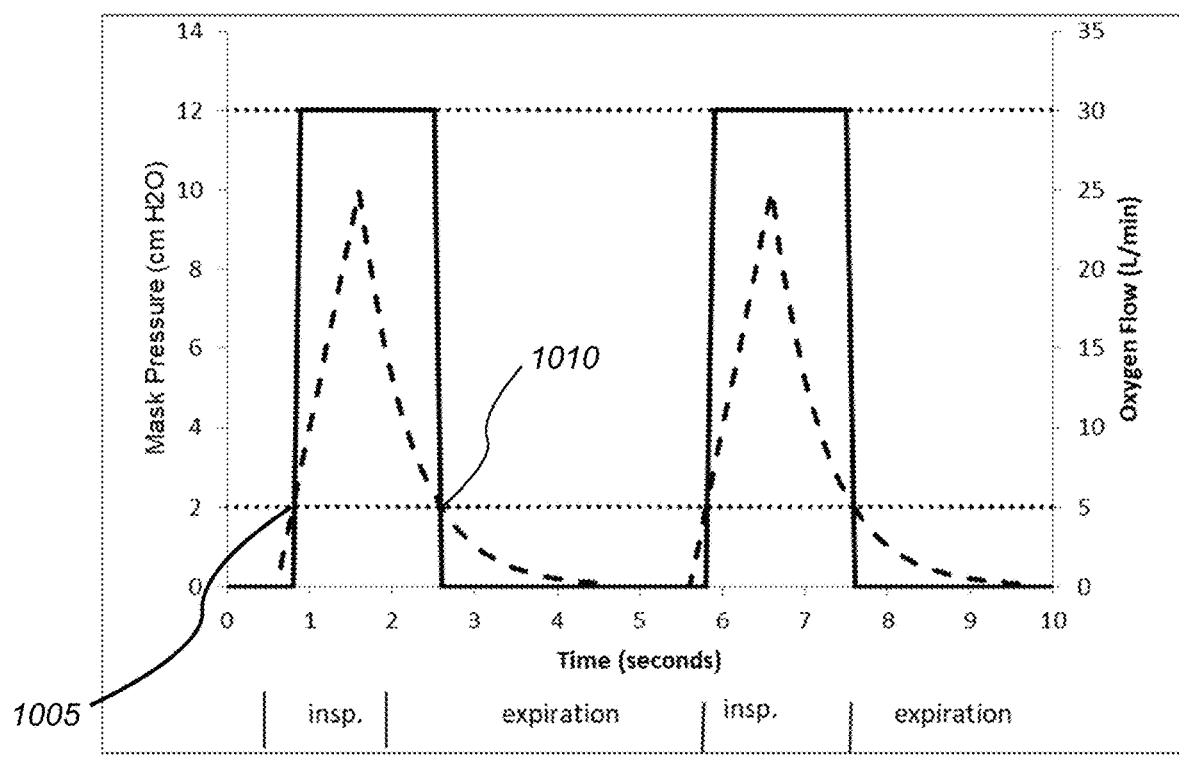
FIG. 10 shows an exemplary log of intra nasal pressures over time, and changes in oxygen flow rate in response thereto.
Figure 11:
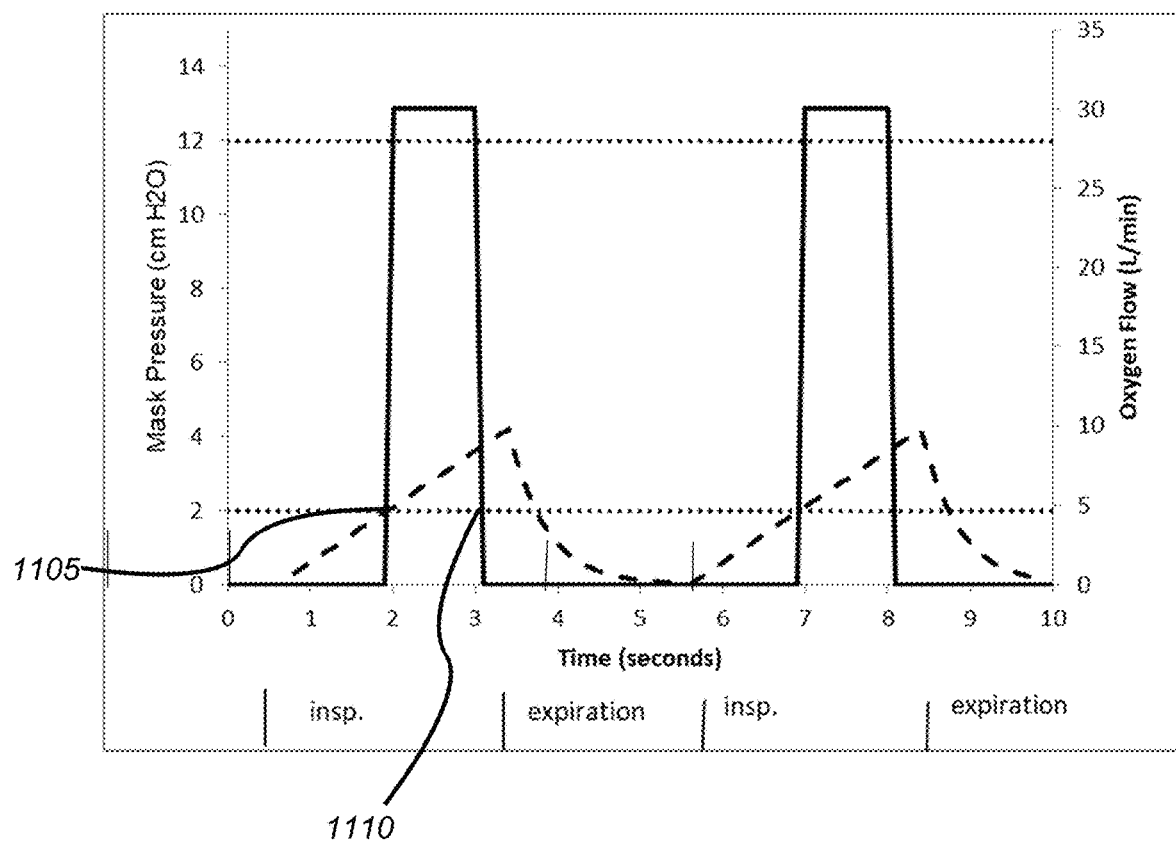
FIG. 11 shows an exemplary log of intra nasal pressures over time, and changes in oxygen flow rate in response to time.
Figure 12:
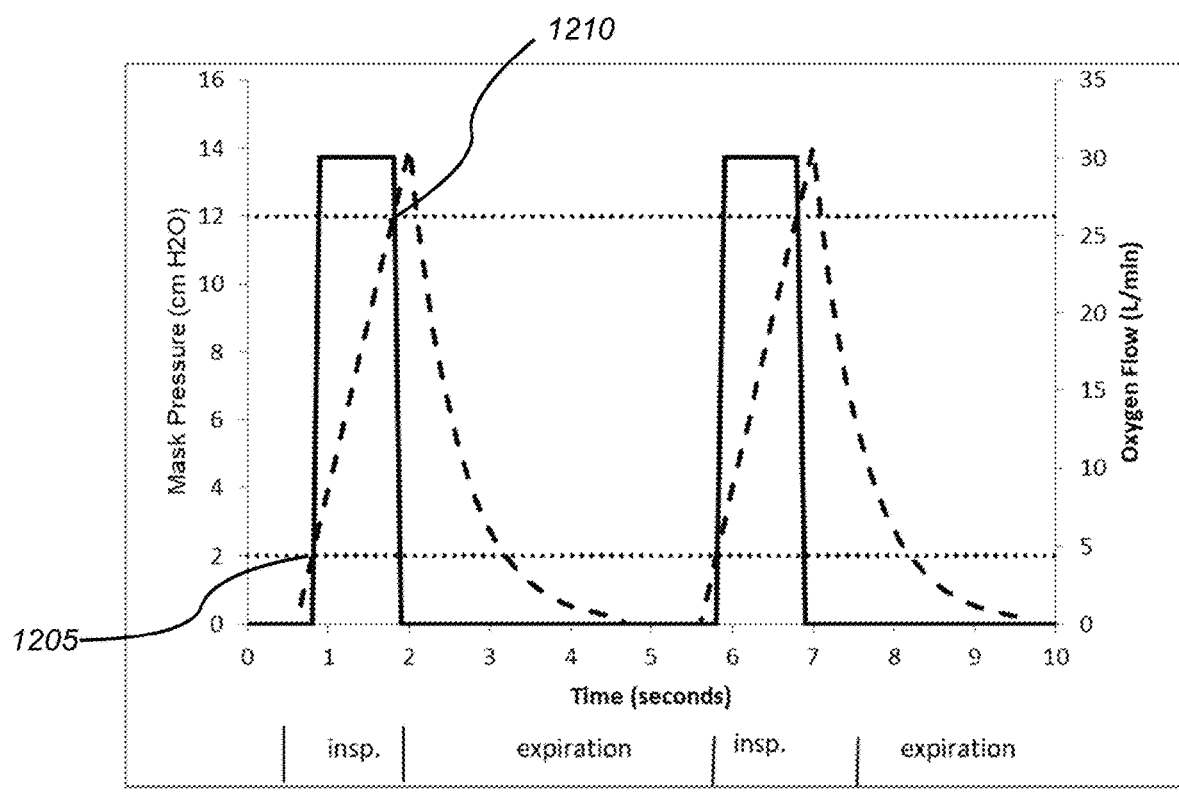
FIG. 12 shows an exemplary log of intra nasal pressures over time, and changes in oxygen flow rate in response to time.

FIGS. 9-12 shows an exemplary logs of the intra-nasal pressures (intra-nasal pressures indicated in dashed lines), as measured by pressure sensor 30, over time, and shows how the oxygen flow (oxygen flow indicated in solid lines) may change in response to various triggers, such as in response to pressure dropping 1 to 5 cm $H_2O$ below the largest positive intra-nasal pressure value (FIG. 9), the pressure dropping below the lower threshold (FIG. 10), a specific time threshold being reached (FIG. 11), and/or the upper threshold being reached (FIG. 12).

Figure 9:
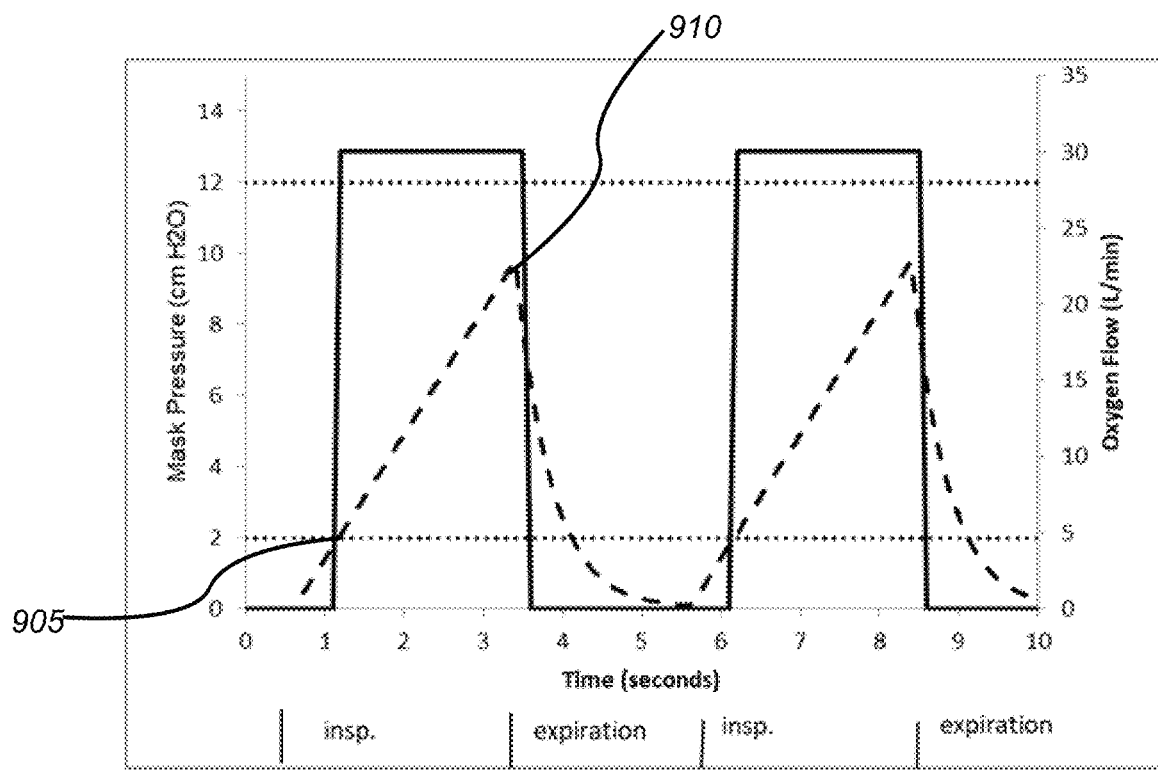
FIG. 9 shows an exemplary log of intra nasal pressures over time, and changes in oxygen flow rate in response thereto.

FIG. 9 shows an exemplary log of the intra-nasal pressures (in dashed lines), as measured by pressure sensor 30, over time, and shows how the oxygen flow (in solid lines) may change in response to the intranasal pressure value reaching the lower threshold limit (as indicated at 905), and in response to the intra-nasal pressure value reached a value within 1 to 5 cm $H_2O$, or 5-30%, less than the highest positive intra-nasal pressure value (i.e., the peak of the inhalation) observed during the breath (as indicated at 910 in FIG. 9). This exemplary log may occur when, for example, the logic of FIG. 6 turns on the high flow of oxygen in response to an intra-nasal pressure above the lower threshold, and then turns off the high flow of oxygen in response to the intra-nasal pressure value reached a value 1-5 cm $H_2O$ (5-30%) less than the highest positive intra-nasal pressure value observed during the breath (as indicated at 620 in FIG. 6).

FIG. 10 shows an exemplary log of the intranasal pressure over time, as measured by pressure sensor 30. Oxygen flow (in solid lines) may be turned on at 1005 when the intranasal pressure value (in dashed lines) reaches a value at or above the lower threshold, as indicated as 1005. Then, when the intranasal pressure value falls below the lower threshold, as indicated at 1010, the oxygen flow may be automatically shut off.

FIG. 11 shows an exemplary log of the intra-nasal pressures, as measured by pressure sensor 30, over time, and shows how the oxygen flow (in solid lines) may change in response to the intranasal pressure value (in dashed lines) reaching the lower threshold limit (as indicated at 1105), and in response to the time reaching the predetermined maximum amount of time for high oxygen flow (as indicated at 1110). In FIG. 11, the exemplary maximum amount of time is 1 second for delivery of high oxygen flow.

FIG. 12 shows an exemplary log of the intra-nasal pressures, as measured by pressure sensor 30. The high flow of oxygen may be turned on in response to the pressure being at or greater than the lower threshold limit (1205). The system may then automatically shut off the high flow of oxygen when the intranasal pressure reaches the upper threshold value (1210). This exemplary log may occur when, for example, the logic of FIG. 5 turns on the high flow of oxygen in response to an intra-nasal pressure above the lower threshold, and then turns off the high flow of oxygen in response to the intranasal pressure value reaching the upper threshold value.

In the specific configurations show in FIGS. 9-12, the lower threshold limit is set at 2 cm $H_2O$ and the upper threshold is set at 12 cm $H_2O$. These specific values are given by way of example, and other values may be used. A clinician may select these values based on the specific patient, or various default values may be used.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A system for delivering oxygen to a patient during a manual mask ventilation process, the system comprising:
   a nasal cannula comprising a first lumen to convey oxygen from a pressurized oxygen source to the patient's nares,
   a second lumen,
   a pressure sensor in communication with the second lumen, the pressure sensor configured to determine an intra-nasal pressure value;
   an electronic oxygen flow valve in communication with a processor, the electronic oxygen flow valve between the pressurized oxygen source and the first lumen of the nasal cannula;
   a mask to be positioned over the nasal cannula, nose and lips of the patient, the mask for manually delivering oxygen to the patient, the mask configured to, when in place, create a seal between a face of the patient and the mask such that oxygen is routed into lungs of the patient;
   the processor programmed to receive the intra-nasal pressure value from the pressure sensor in communication with the second lumen;
   the processor programmed to compare the intra-nasal pressure value to a pre-determined oxygen flow activation threshold pressure value; and
   the processor programmed to adjust the electronic oxygen flow valve to deliver a pre-determined high oxygen flow through the first lumen when the processor determines gas is being manually delivered to the patient when the intra-nasal pressure value is greater than the pre-determined oxygen flow activation threshold pressure value.

2. The system of claim 1, wherein the pre-determined high oxygen flow is between about 10 liters to about 40 liters per minute.

3. The system of claim 1, wherein the pre-determined oxygen flow activation threshold pressure value is greater than 2 cm $H_2O$.

4. The system of claim 1, wherein the processor is further programmed to, after the processor has adjusted the electronic oxygen flow valve to deliver the pre-determined high oxygen flow, compare the intra-nasal pressure value to a pre-determined high pressure threshold value, and
   the processor programmed to adjust the electronic oxygen flow valve to turn off oxygen flow through the first lumen when the processor determines the intra-nasal pressure value is greater than the pre-determined high pressure threshold value.

5. The system of claim 4, wherein the pre-determined high pressure threshold value is between about 12 cm $H_2O$ and about 15 cm $H_2O$.

6. The system of claim 1, wherein the processor is further programmed to, after the processor has adjusted the electronic oxygen flow valve to deliver the pre-determined high oxygen flow, compare the intra-nasal pressure value to a pre-determined high pressure alarm threshold value and the processor programmed to adjust the electronic oxygen flow valve to turn off all oxygen flow through the first lumen, when the processor determines the intra-nasal pressure value is greater than the pre-determined high pressure alarm threshold value.

7. The system of claim 6, wherein the processor is further programmed to activate an alarm when the processor determines the intra-nasal pressure value is greater than the pre-determined high pressure alarm threshold value.

8. The system of claim 1, wherein the processor is further programmed to, after the processor has adjusted the electronic oxygen flow valve to deliver the pre-determined high oxygen flow through the first lumen, compare a current intra-nasal pressure value to the pre-determined oxygen flow activation threshold pressure value, and
   wherein the processor is further programmed to adjust the electronic oxygen flow valve to turn off the pre-determined high oxygen flow through the first lumen when the processor determines the intra-nasal pressure value is lower than a pre-determined low pressure threshold.

9. The system of claim 8, wherein the system further comprises a nasal cannula having a third lumen, and wherein the system further comprises a capnometry device to measure an end-tidal $CO_2$ value, the capnometry device in connection with the third lumen of the nasal cannula, and wherein the processor is further programmed to receive an end-tidal $CO_2$ measurement from the capnometry device after the processor has adjusted the electronic oxygen flow valve to turn off the pre-determined high oxygen flow through the first lumen.

10. The system of claim 9, wherein the processor is further programmed to adjust the electronic oxygen flow valve to turn on a pre-determined low oxygen flow through the first lumen after the processor has received the end-tidal $CO_2$ measurement from the capnometry device, the pre-determined low oxygen flow configured to flush exhaled $CO_2$ from the mask.

11. The system of claim 10, wherein the processor is further programmed to adjust the electronic oxygen flow valve to turn on the pre-determined low oxygen flow through the first lumen after a pre-determined amount of time for exhalation has passed after the processor adjusted the electronic oxygen flow valve to turn off the pre-determined high oxygen flow through the first lumen.

12. The system of claim 11, wherein the pre-determined amount of time for exhalation is about 1 second.

13. The system of claim 8, wherein the pre-determined low pressure threshold is equal to the pre-determined oxygen flow activation threshold pressure value.

14. The system of claim 1, wherein the processor is further programmed to, after the processor has adjusted the electronic oxygen flow valve to deliver the pre-determined high oxygen flow through the first lumen, receive, at the processor, an amount of time the electronic oxygen flow valve has delivered the pre-determined high oxygen flow through the first lumen;
wherein the processor is programmed to compare the amount of time the electronic oxygen flow valve has delivered the pre-determined high oxygen flow rate through the first lumen with a pre-determined maximum amount of time for high oxygen flow rate delivery; and
wherein the processor is programmed to adjust the electronic oxygen flow valve to turn off the pre-determined high oxygen flow through the first lumen when the processor determines the amount of time the electronic oxygen flow valve has delivered the pre-determined high oxygen flow through the first lumen is greater than the pre-determined maximum amount of time for high oxygen flow rate delivery.

15. The system of claim 14, wherein the second lumen comprises a high-flow oxygen cannula for connection to a source of high pressure oxygen, and further comprising a pressure sensor in communication with the oxygen cannula, the pressure sensor configured to determine an intra-nasal pressure value.

16. The system of claim 1, wherein a pre-determined maximum amount of time for high oxygen flow rate delivery is between 0.5 seconds and 2.5 seconds.

17. The system of claim 1, wherein the processor is programmed to receive and store a plurality of intra-nasal pressure values over time, and wherein the processor is further programmed to compare each of the plurality of intra-nasal pressures values to the pre-determined oxygen flow activation threshold pressure value to determine a time which a manual ventilation sequence has begun, and
wherein the processor is further programmed to receive an amount of time passed since the manual ventilation sequence has begun, and
wherein the processor is further programmed to compare the amount of time passed to a predetermined maximum time value, and
wherein the processor is further programmed to send an alert to an output device if the amount of time passed is greater than the predetermined maximum time value.

18. The system of claim 17, wherein the processor is further programmed to compare the amount of time passed to a predetermined minimum time value, and
wherein the processor is further programmed to send an alert to an output device if the amount of time passed is less than the predetermined minimum time value.

19. The system of claim 1, wherein the processor is further programmed to receive and store a plurality of intra-nasal pressure values from the pressure sensor to create an intra-nasal pressure log;
the processor programmed to analyze each of the plurality of intra-nasal pressure values of the intra-nasal pressure log to determine if a breath has been given to the patient during a pre-determined amount of time; and
the processor further programmed to adjust the electronic oxygen flow valve to deliver the pre-determined high oxygen flow through the first lumen when the processor determines no breath has been given to the patient during the pre-determined amount of time.

20. The system of claim 19, wherein the pre-determined amount of time is between about 5 seconds and about 30 seconds.

21. The system of claim 1, wherein the processor is further programmed to receive and store a plurality of intra-nasal pressure values from the pressure sensor to create an intra-nasal pressure log;
the processor programmed to analyze each of the plurality of intra-nasal pressure values of the intra-nasal pressure log to determine the largest positive intra-nasal pressure value measured by the pressure sensor for a breath cycle; and
the processor further programmed to adjust the electronic oxygen flow valve to shut off the pre-determined high oxygen flow through the first lumen when the processor determines the intra-nasal pressure value has dropped below the largest positive intra-nasal pressure value.

22. The system of claim 21, wherein the processor is further programmed to adjust the electronic oxygen flow valve to shut off the pre-determined high oxygen flow through the first lumen when the processor determines the intra-nasal pressure value has dropped between 1 and 5 cm $H_2O$ below the largest positive intra-nasal pressure value.

23. The system of claim 21, wherein the processor is further programmed to adjust the electronic oxygen flow valve to shut off the pre-determined high oxygen flow through the first lumen when the processor determines the intra-nasal pressure value has dropped between 1 and 5 cm $H_2O$ below the largest positive intra-nasal pressure value.

24. The system of claim 1, wherein the processor is further programmed to receive and store a plurality of intra-nasal pressure values from the pressure sensor to create an intra-nasal pressure log;
the processor programmed to analyze each of the plurality of intra-nasal pressure values of the intra-nasal pressure log to determine the largest positive intra-nasal pressure value; and
the processor further programmed to adjust the electronic oxygen flow valve to shut off the pre-determined high oxygen flow through the first lumen when the processor determines the intra-nasal pressure value has dropped more than 5% lower than the largest positive intra-nasal pressure value.

25. A method for delivering oxygen to a patient during a manual mask ventilation process, the method comprising:
- positioning a nasal cannula in the patient's nares, the nasal cannula comprising a first lumen to convey oxygen from a pressurized oxygen source to the patient's nares and a second lumen in communication with a pressure sensor configured to determine an intranasal pressure value;
- detecting the patient's intra-nasal pressure value at discrete times to determine a plurality of intranasal pressure values over time, and receiving the plurality of intra-nasal pressure values at a processor;
- the processor analyzing the plurality of intra-nasal pressure values to determine if a manual ventilation breath is being given, and when the processor determines a manual ventilation breath is being given, the processor communicating with a flow valve to deliver a high-flow pulse of oxygen.

26. The method of claim 25, further comprising the step of positioning a mask over the nasal cannula, a nose and lips of the patient, the mask for manually delivering oxygen to the patient, the mask configured to, when in place, create a seal between the nose and lips of the patient and the mask such that oxygen is routed into lungs of the patient.

27. The method of claim 26, further comprising the step of, after the processor determines a manual ventilation breath is being given and the processor communicates with the flow valve to deliver the high-flow pulse of oxygen,
- the processor comparing the intra-nasal pressure value to a pre-determined high pressure threshold value, and the processor adjusting the flow valve to turn off all oxygen flow through the first lumen when the processor determines the intra-nasal pressure value is greater than the pre-determined high pressure threshold value.

28. A system for delivering oxygen to a patient during a manual mask ventilation process, the system comprising:
- a nasal cannula;
- means to convey oxygen from a pressurized oxygen source to the patient's nares,
- a pressure sensor configured to determine an intra-nasal pressure value;
- an electronic oxygen flow valve in communication with a processor, the electronic oxygen flow valve between the pressurized oxygen source and the means to convey oxygen to the patient's nares;
- a mask to be positioned over the nasal cannula, nose and lips of the patient, the mask for manually delivering oxygen to the patient, the mask contoured to, when in place, create a seal around the nose and lips of the patient and the mask such that oxygen is routed into lungs of the patient;
- the processor programmed to receive the intra-nasal pressure value from the pressure sensor;
- the processor programmed to compare the intra-nasal pressure value to a pre-determined oxygen flow activation threshold pressure value; and
- the processor programmed to adjust the electronic oxygen flow valve to deliver a pre-determined high oxygen flow through the means to convey oxygen from the pressurized oxygen source to the patient's nares when the processor determines gas is being manually delivered to the patient when the intra-nasal pressure value is greater than the pre-determined oxygen flow activation threshold pressure value.

\* \* \* \* \*